(12) United States Patent
Hoganson et al.

(10) Patent No.: US 12,186,128 B2
(45) Date of Patent: *Jan. 7, 2025

(54) VALVE COAPTATION MEASUREMENT DEVICES

(71) Applicant: Children's Medical Center Corporation, Boston, MA (US)

(72) Inventors: David M. Hoganson, Brookline, MA (US); Peter E. Hammer, Needham, MA (US)

(73) Assignee: Children's Medical Center Corporation, Boston, MA (US)

( * ) Notice: Subject to any disclaimer, the term of this patent is extended or adjusted under 35 U.S.C. 154(b) by 56 days.

This patent is subject to a terminal disclaimer.

(21) Appl. No.: 18/083,050

(22) Filed: Dec. 16, 2022

(65) Prior Publication Data

US 2023/0225703 A1 Jul. 20, 2023

Related U.S. Application Data

(63) Continuation of application No. 16/755,015, filed as application No. PCT/US2018/055920 on Oct. 15, 2018, now Pat. No. 11,553,893.

(Continued)

(51) Int. Cl.
*A61B 8/08* (2006.01)
*A61B 1/00* (2006.01)
(Continued)

(52) U.S. Cl.
CPC ........ *A61B 8/0883* (2013.01); *A61B 1/00045* (2013.01); *A61B 1/07* (2013.01);
(Continued)

(58) Field of Classification Search
CPC ..... A61B 8/0883; A61B 1/00045; A61B 1/07; A61B 5/02; A61B 5/1072; A61B 5/1076;
(Continued)

(56) References Cited

U.S. PATENT DOCUMENTS 11,553,893 B2   1/2023  Hoganson et al.
2005/0283232 A1 12/2005 Gabbay
(Continued)

FOREIGN PATENT DOCUMENTS

JP   H11-206739 A   8/1999
JP   2005-517510 A  6/2005

OTHER PUBLICATIONS

CN Office Action in Chinese Appln. No. 201880073039.2, dated Nov. 25, 2022, 9 pages (with English translation).
(Continued)

*Primary Examiner* — Joseph M Santos Rodriguez
*Assistant Examiner* — Kaitlyn E Sebastian
(74) *Attorney, Agent, or Firm* — Fish & Richardson P.C.

(57) ABSTRACT

Methods, systems, and cooptation measurement devices as described herein include an elongate sensor body at the end of a proximal connecting member, and a plurality of sensors in an array across a face of the sensor body, wherein each sensor of the plurality of sensors is configured to detect if a portion of a heart valve is in contact with the sensor.

22 Claims, 11 Drawing Sheets

Related U.S. Application Data

(60) Provisional application No. 62/572,034, filed on Oct. 13, 2017.

(51) Int. Cl.

| | |
|---|---|
| *A61B 1/07* | (2006.01) |
| *A61B 5/00* | (2006.01) |
| *A61B 5/02* | (2006.01) |
| *A61B 5/107* | (2006.01) |
| *A61B 8/00* | (2006.01) |
| *A61B 8/12* | (2006.01) |

(52) U.S. Cl.
CPC .............. *A61B 5/02* (2013.01); *A61B 5/1072* (2013.01); *A61B 5/1076* (2013.01); *A61B 5/1079* (2013.01); *A61B 5/743* (2013.01); *A61B 8/12* (2013.01); *A61B 8/445* (2013.01); *A61B 2562/0271* (2013.01); *A61B 2562/043* (2013.01); *A61B 2562/164* (2013.01)

(58) Field of Classification Search
CPC ......... A61B 5/1079; A61B 5/743; A61B 8/12; A61B 8/445; A61B 2562/0271; A61B 2562/043; A61B 2562/164; A61B 5/6885; A61B 5/015; A61B 5/0044; A61B 2503/06; A61B 2562/046; A61B 5/6852; A61B 5/6869
See application file for complete search history.

(56) References Cited

U.S. PATENT DOCUMENTS

| | | |
|---|---|---|
| 2008/0228223 A1 | 9/2008 | Alkhatib et al. |
| 2010/0331883 A1 | 12/2010 | Schmitz et al. |
| 2011/0160596 A1 | 6/2011 | Cecere et al. |
| 2011/0208293 A1 | 8/2011 | Tabor et al. |
| 2014/0180400 A1* | 6/2014 | Bruchman ............ A61F 2/2415 623/2.17 |
| 2014/0213918 A1 | 7/2014 | Venkatasubramanian et al. |
| 2015/0223707 A1 | 8/2015 | Ludolph |
| 2015/0282753 A1 | 10/2015 | Ahmadi et al. |
| 2015/0327997 A1* | 11/2015 | Pollack .................. A61B 34/25 623/2.11 |
| 2020/0345326 A1 | 11/2020 | Hoganson et al. |

OTHER PUBLICATIONS

De Waroux et al., "Mechanisms of recurrent aortic regurgitation after aortic valve repair: predictive value of intraoperative transesophageal echocardiography," JACC: Cardiovascular Imaging, Aug. 1, 2009, 2(8):931-9.
EP Extended European Search Report in European Appln. No. 18867034.3, dated Nov. 9, 2020, 7 pages.
JP Japanese Office Action in Japanese Appln. No. 2020-520736, dated Oct. 25, 2022, 10 pages (with English translation).
PCT International Preliminary Report on Patentability in International Appln. No. PCT/US18/55920, dated Apr. 14, 2020, 6 pages.
PCT International Search Report and Written Opinion in International Appln. No. PCT/US18/55920, dated Dec. 27, 2018, 8 pages.
Stern et al., "Intraoperative echocardiography for congenital aortic valve repair: predictors of early reoperation," The Annals of Thoracic Surgery, Aug. 1, 2015, 100(2):678-85.
Yamauchi et al., "Evaluation of the mitral valve leaflet morphology after mitral valve reconstruction with a concept coaptation length index," Journal of Cardiac Surgery, Sep. 2005, 20(5):432-5.
CN Office Action in Chinese Appln. No. 201880073039.2, mailed on Jun. 5, 2023, 10 pages (with English translation).
CN Office Action in Chinese Appln. No. 201880073039.2, mailed on Jan. 5, 2024, 6 pages (with English translation).
EP Office Action in European Appln. No. 18867034.3, mailed on Apr. 15, 2024, 5 pages.

* cited by examiner

VALVE COAPTATION MEASUREMENT DEVICES

CROSS REFERENCE TO RELATED APPLICATIONS

This application is a continuation of claims priority to U.S. application Ser. No. 16/755,015, filed Apr. 9, 2020, which is a 371 U.S. National Phase of PCT/US2018/055920, filed on Oct. 15, 2018, which claims priority under 35 U.S.C. § 120 from U.S. Provisional Application No. 62/572,034 filed on Oct. 13, 2017. The entire contents of the priority application are incorporated herein by reference.

TECHNICAL FIELD

This invention relates to the assessment of the coaptation height of a heart valve during surgery or another interventional procedure.

BACKGROUND OF THE INVENTION

Assessment of heart valve function is currently accomplished by a variety of modalities. In the evaluation of a patient with heart valve disease, an echocardiogram is often the principle assessment tool for assessing the function of a heart valve. Each of the four major valves (the aortic valve, pulmonary valve, mitral valve, and tricuspid valve) have particular associated anatomical and functional characteristics. As these valves are assessed by echocardiogram, the degree of regurgitation or backward flow as well as stenosis or impairment to forward flow are important aspects of the valve function. Valves that are not functioning adequately may have one or more of several different mechanisms causing the poor function. For valves that are regurgitant or leaking, a lack of adequate and stable coaptation between adjacent heart valve leaflets is often the fundamental reason for the leakage through the valve. The exact mechanism for lack of adequate coaptation can vary and can include issues with the support structure below the valve (the subvalvar apparatus), issues with leaflets, or issues with the support structure around the valve (the annulus).

Coaptation is where the valve leaflets contact each other to create the valve seal and it is expressed as coaptation height. This height refers to the distance over which adjacent valve leaflets touch each other to close off the valve and prevent regurgitation through the valve. The taller the coaptation height, the better the valve will likely function in the short and long-term. The coaptation height between two leaflets can vary along the entire coaptation surface between two leaflets of the valve, and between different leaflet parings of the valves that have more than two leaflets.

Assessment of the coaptation height prior to any intervention on the valve has typically been done by echocardiogram. This is done with some frequency in adult valves where the leaflet tissues are thicker and coaptation height can be more easily imaged and often measured. In pediatric heart valves, the leaflets are thinner, often making it difficult to measure coaptation height by echocardiogram (ECHO), especially for the atrioventricular valves. Reports from adult and pediatric cardiac surgery literature cite the coaptation height as being an important predictor of function after valve repair.

SUMMARY OF THE INVENTION

This disclosure relates to methods of assessing heart valves by measuring the coaptation height of the heart valve across the coaptation surface. In some aspects, the disclosure relates to devices with multiple sensors placed across the valve. The valve is then forced to coapt either through passive testing by closing the valve under the force of a fluid injected into the ventricle or aortic root, or by testing the valve under normal physiologic circumstances with the heart beating. The coaptation height of the valve is measured across one or more points using multiple sensors integrated into the distal aspect of the device. The coaptation height is displayed for the user and the user can track the coaptation height of the valve along one or more points on the coaptation surface. The surgeon or operator may use the coaptation height information to assess the valve for decision-making purposes regarding a possible intervention or for feedback regarding the adequacy of the valve before, during, or after valve repair surgery.

In one embodiment, a multisensor array on the distal aspect of the device is placed across the valve extending into the heart chamber or great vessel past the valve as well as extending into the heart chamber or great vessel proximal to the valve. The distal aspect of the device may be relatively rigid or may be flexible, even flexible enough to be displaced by the valve as it closes. The width of the distal aspect of the coaptation measurement device may be narrow such that only a numerical coaptation height is generated as information from the device. In another embodiment, the width of the distal aspect of place may be several millimeters or up to several centimeters wide and the coaptation height of the valve is displayed as multiple numerical points as well as a graphical display of the coaptation height along the portion of the coaptation surface which is measured.

The coaptation measurement device may be mounted in a catheter-based device that can be placed across a valve during catheterization procedure while the heart is beating. In another embodiment, the catheter-based coaptation device can be utilized during an operation where the surgeon passes it across a valve while the heart is beating after the patient has been weaned from a heart lung machine. The catheter-based coaptation measurement device can access all of the heart valves and measure the coaptation height along the coaptation surface in one or more physiologic conditions. The coaptation measurement device can provide information for decision-making regarding possible intervention or re-intervention for one or more of the heart valves.

In some embodiments, a coaptation measurement device includes an elongate sensor body at the end of a proximal connecting member, and a plurality of sensors in an array across a face of the sensor body, wherein each sensor of the plurality of sensors is configured to detect if a portion of a heart valve is in contact with the sensor.

Implementations can include one or more of the following: a plurality of sensors are arranged across a second face of the sensor body. Each sensor of the plurality of sensors has a width of a least a half of a width of the elongate sensor body. The elongate sensor body is flexible. The elongate sensor body is between several millimeters and several centimeters wide. The plurality of sensors includes resistor elements or temperature-sensing elements. The plurality of sensors includes fiberoptic elements or ultrasound elements. The array is a capacitor array.

In some embodiments, a method of measuring a coaptation height of a heart valve across a coaptation surface includes placing a coaptation measurement device next to a coaptation surface, the coaptation device comprising: an elongate sensor body at the end of a proximal connecting member, and a plurality of sensors in an array across a face of the sensor body. Each sensor of the plurality of sensors is configured to detect if a portion of a heart valve is in contact with the sensor, causing or allowing the valve to close, detecting which sensors of the plurality of sensors detect that the respective sensor is in contact with the heart valve, and determining a coaptation height from the sensors.

Implementations can include one or more of the following: displaying the determined coaptation height. Repeating the placing, causing, detecting, and determining steps along one or more points on a coaptation surface. Displaying the determined height at each point on the coaptation surface as numerical values or as a graphical display. Causing the valve to close comprises injecting fluid into a ventricle or aortic root. The plurality of sensors includes resistor elements or temperature-sensing elements. The plurality of sensors includes fiberoptic elements or ultrasound elements. The array is a capacitor array.

In some embodiments, a coaptation measurement system includes a coaptation measurement device, comprising an elongate sensor body at the end of a proximal connecting member; and a plurality of sensors in an array across a face of the sensor body, wherein each sensor of the plurality of sensors is configured to detect if a portion of a heart valve is in contact with the sensor, an extension member attachable to the proximal connecting member, a handle connected to the extension member; and a display connected to the device, wherein the display is configured to show information detected by the sensors of the coaptation measurement device.

Implementations can include one or more of the following: the extension member is malleable or bendable. A plurality of sensors are arranged across a second face of the sensor body. Each sensor of the plurality of sensors has a width of a least a half of the width of the elongate sensor body. The elongate sensor body is flexible. The plurality of sensors includes resistor elements or temperature-sensing elements. The plurality of sensors includes fiberoptic elements or ultrasound elements. The array is a capacitor array.

The advantages and other features of the technology disclosed herein will become more readily apparent to those having ordinary skill in the art and the following detailed description of certain embodiments in conjunction with the drawings that set forth representative embodiments of the present invention and wherein like reference numerals identify similar structural elements. It is to be understood that the subject technology is not intended to be limited to the particular constructs and methods described in the described embodiments, as one skilled in the art can extend the concepts involving involved using variations that are obvious after reading the present disclosure. All publications, patent applications, patents, and other references mentioned herein are incorporated by reference into their in their entirety. In the case of conflict, the present specification, including definitions, will control. In addition, the materials methods, and examples are illustrative only and not intended to be limiting. All relative descriptions herein, such as top, bottom, left, right, up, and down are with reference to the figures, and not meant to be in a limiting sense.

DETAILED DESCRIPTION

The present disclosure overcomes many of the challenges associated with measurement of coaptation height in the assessment of heart valves using known methods. The coaptation measurement devices described herein are placed across a heart valve during a catheterization procedure or open surgical assessment of the valve. The coaptation measurement devices can quantify the coaptation height of the valve along the coaptation surface of the valve. This coaptation height measurement can be assessed along the coaptation surface of the valve to determine various aspects of the valve and provide valuable information for the cardiologist in the catheter lab or the surgeon who is assessing and/or repairing the heart valve. Coaptation height information may be used to guide as well as adjust and assess the adequacy of a valve intervention.

Assessment of coaptation height during surgery while a valve is being actively repaired has been limited to qualitative approaches, frequently involving staining exposed leaflets with ink and assessing other portions of the valve that remain unstained. These techniques are not applicable to all valves and have some inherent limitations. Prior qualitative methodology of assessing valves during repairs as part of open-heart surgery often involves a qualitative assessment of the ability the valve to prevent saline from leaking through a ventricle. During testing of an atrioventricular valve while the heart is open, saline or a similar buffered crystalloid solution is injected into the ventricle to distend the ventricle and close the valve. This is referred to as passive testing. For aortic valve repairs, the aortic root is filled and the coaptation of the valve qualitatively assessed albeit with very low pressure. These methodologies do not give any assessment of quantitative coaptation height along the portion of the valve. Although coaptation height is fundamental to the function of the valve and in some reports is predictive of later outcome of valve function, it is difficult to assess during an operation or another interventional procedure.

Figure 1A:
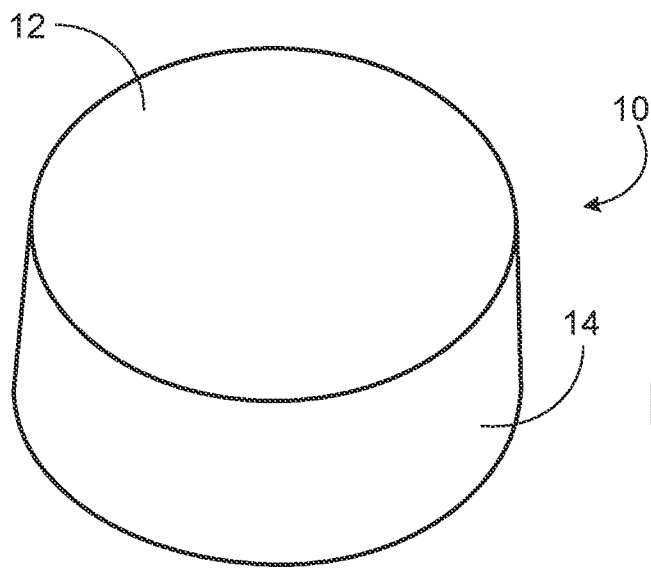
FIG. 1A is a view of a mitral valve from the perspective of the left atrium looking towards the left ventricle.

Referring to FIG. 1A, a mitral valve 10 is shown as viewed from the left atrium. The mitral valve 10 has an anterior leaflet 12 and posterior leaflet 14. The anterior 12 and posterior 14 leaflets press against each other during systole as a left ventricle squeezes to prevent regurgitation of blood from the left ventricle into the left atrium. Referring to FIG. 1B, a cross-sectional image of the left ventricle is shown, with left ventricular wall 18 and left ventricular cavity 17, and with the anterior leaflet of the mitral valve 12 and posterior leaflet of the mitral valve 14 separating the left ventricle from the left atrium. The cord support structures of the mitral valve leaflets 16 are essential for the normal function of the mitral valve. The degree to which the anterior-posterior leaflets touch each other as a valve closes the coaptation of the valve. The coaptation can be measured as a coaptation as shown by arrow 20 in FIG. 1B.

Figure 1C:
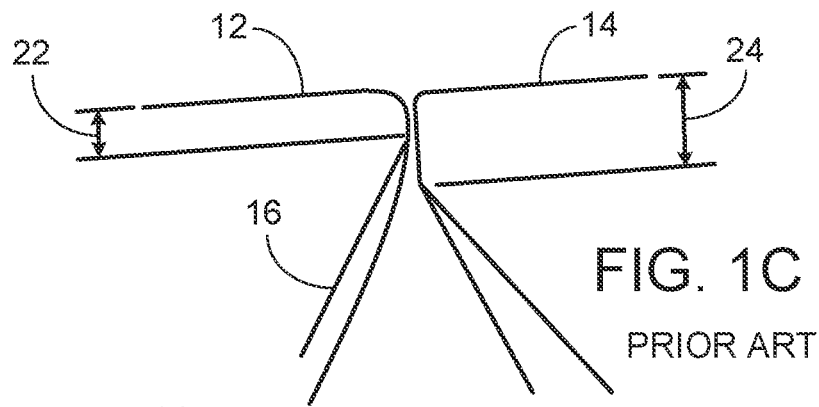
FIG. 1C is a cross-sectional view of a mitral valve during diastole.
Figure 1B:
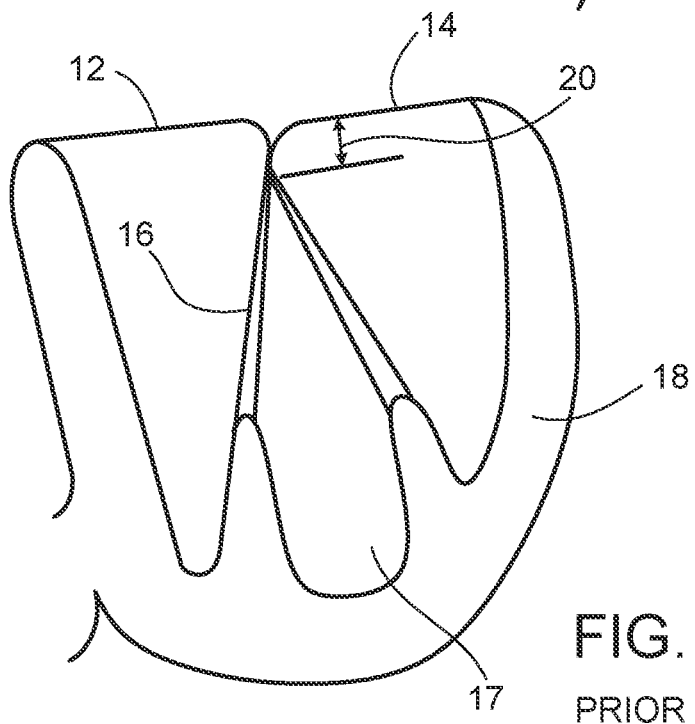
FIG. 1B is a cross-sectional view of the left ventricle with mitral valve leaflets and subvalvar apparatus.

Referring to FIG. 1C, the anterior leaflet of a mitral valve 12 and posterior leaflet 14 may be altered from their normal function such that one or the other of the leaflets does not come to the middle and coapt normally. This may result in a difference in the amount of the valve leaflet material available for coaptation. This may result in one valve leaflet, such as the anterior leaflet 12, having a potential coaptation height shown by arrow 22 while the posterior leaflet 14 has a potential coaptation height that is different shown by arrow 24. As heart valves are being assessed either prior, during, or after a valve intervention or repair, knowing both the height of actual coaptation where the valve leaflets touch each other (spanned by arrow 22) as well as the available valve leaflet material for coaptation (spanned by arrow 24) for the posterior leaflet in the event that they are different is very useful. This is very useful information in assessing and eventually intervening on a valve.

Figure 1D:
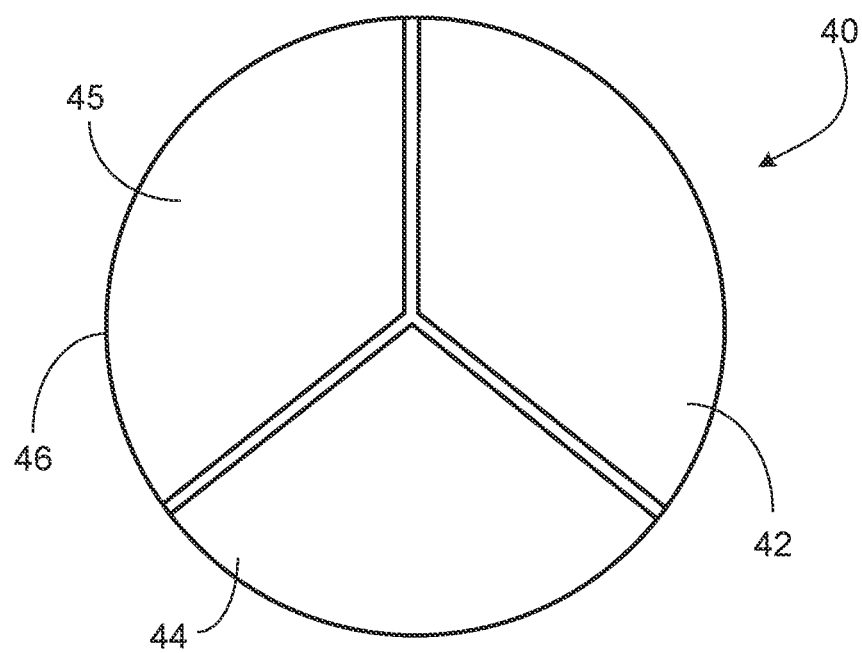
FIG. 1D is a view of an aortic valve from the perspective of the aortic root looking down toward the left ventricle.
Figure 1E:
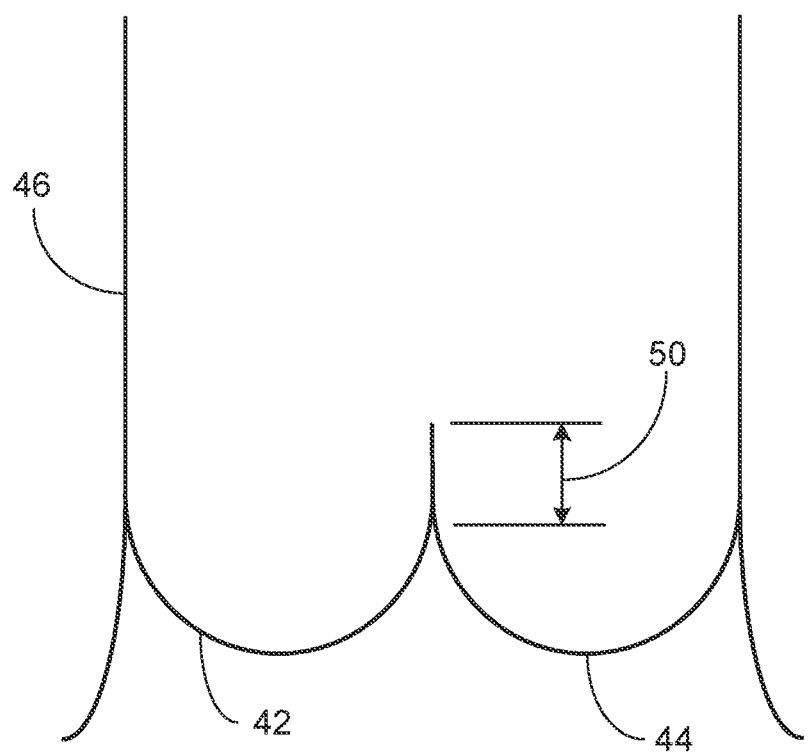
FIG. 1E is a cross-sectional view of the aortic valve and aortic root.
Figure 1F:
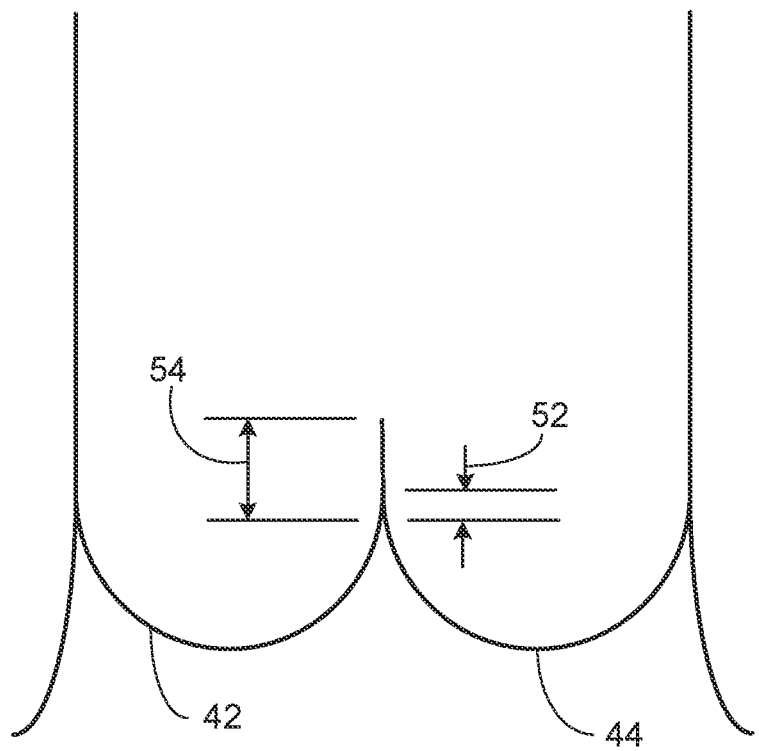
FIG. 1F is a cross-sectional view of an aortic valve and aortic root.

Referring to FIG. 1D, an aortic valve is shown as viewed from the aortic root looking down towards the left ventricle. This aortic valve 40 has three valve parts, which are leaflets 42, 44, 45 and which are constrained by the aortic root wall 46. Referring to FIG. 1E, a cross-section of the aortic valve, valve leaflets 42 and 44 are constrained by the aortic root wall 46. The height of coaptation of the adjacent aortic valve leaflets 42 and 44 is shown as a measurable height 50. Referring to FIG. 1F, a cross-sectional view of an aortic valve with leaflets 42 and 44 demonstrates various potential heights 52 and 54 that may result in a functional coaptation height of the valve depending on how the valve is intervened upon. In this current valve, the functional or actual coaptation height would be 52.

Figure 2A:
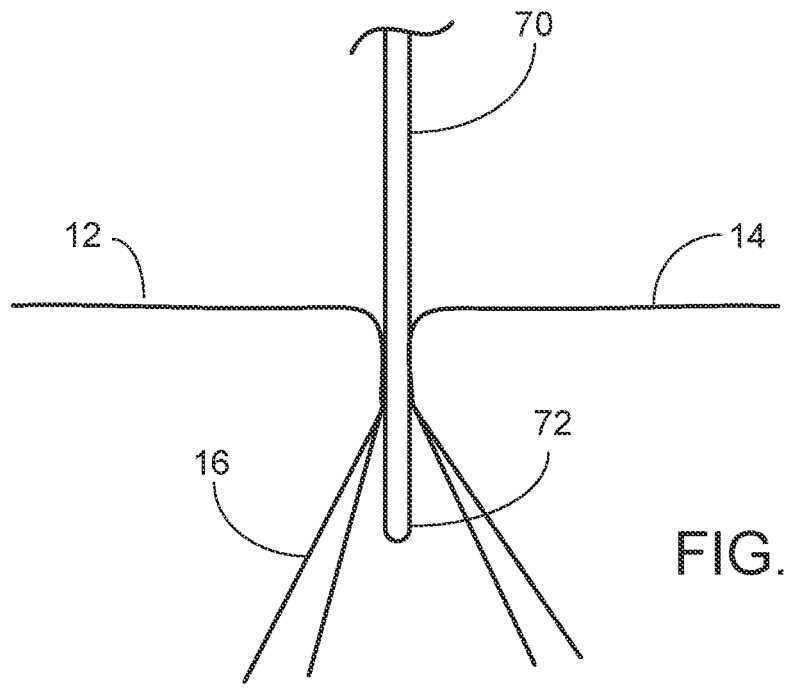
FIG. 2A is a cross-sectional view of a mitral valve and subvalvar apparatus with a coaptation measurement device across the valve.

FIG. 2A shows a mitral valve in cross-section with anterior leaflet 12 and posterior leaflet 14, with subvalvar chordal attachments 16, and with a coaptation measurement device 70 with an elongated distal portion 72. The coaptation measurement device 70 is positioned across the mitral valve between leaflets 12 and 14, with its distal end 72 arranged within the left ventricle.

The coaptation measurement device 70 is placed across a heart valve during a catheterization procedure or open surgical assessment of the valve. The coaptation measurement device 70 can quantify the coaptation height of the valve by assessment of the coaptation surface of the valve. This coaptation height measurement can be assessed along the coaptation surface of the valve across the aspects of the valve to provide valuable information for the cardiologist in the catheterization lab or the surgeon who is assessing and/or repairing the heart valve. Coaptation height information can be used to guide as well as adjust and assess the adequacy of a valve intervention.

The coaptation measurement device 70 has sensors built into the device to assess the degree of coaptation of the valve in the area of the valve across which the device was placed. By differentiating between the left atrium, the coaptation portion of the valve, and the left ventricle, the height of coaptation can be measured. The coaptation measurement device 70 can have sensors on one or both sides to assess the valve coaptation height. If there are sensors on both sides, the valve coaptation height can be assessed as the smaller of the coaptation height of each leaflet. A leaflet with a taller height can be viewed as potential for more coaptation if the valve leaflets were to be moved in by some valve intervention.

Figure 2B:
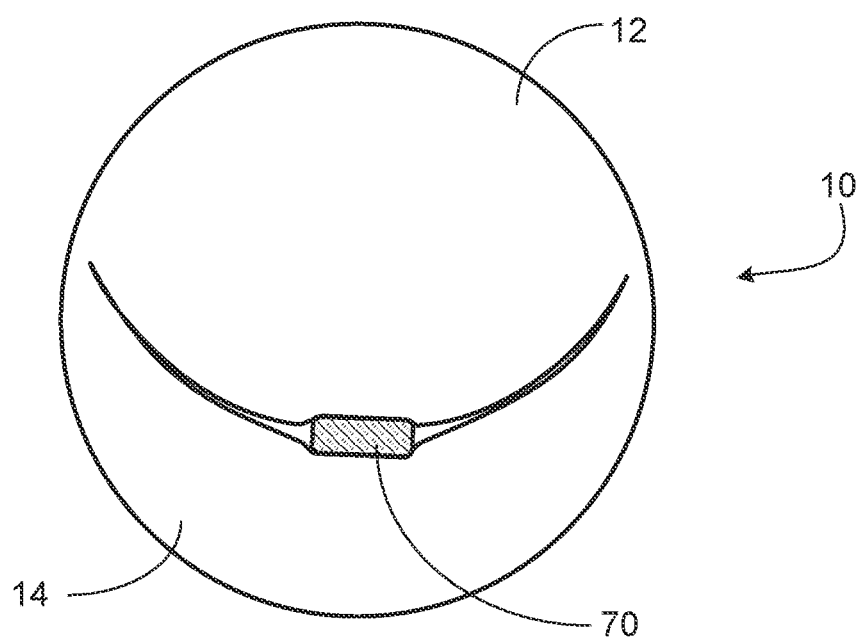
FIG. 2B is a view of the mitral valve from the perspective of the left atrium with a coaptation measurement device across the valve.
Figure 2C:
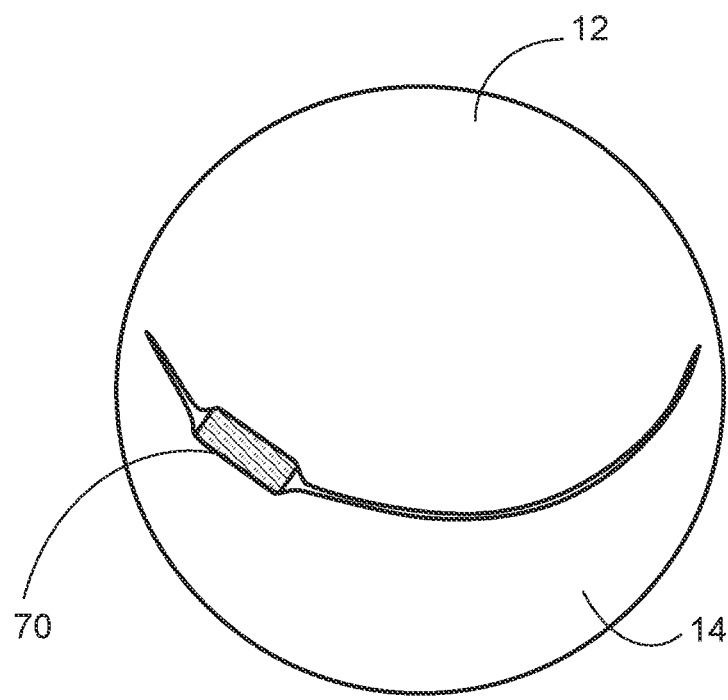
FIG. 2C is a view of the mitral valve from the perspective of the left atrium with a coaptation measurement device across the valve.

Referring to FIG. 2B, a mitral valve 10 is shown from the perspective of the left atrium looking toward the left ventricle. The anterior leaflet 12 and posterior leaflet 14 have a coaptation measurement device 70 shown in cross-section, which extends between the anterior leaflet 12 and posterior leaflet 14. The coaptation measurement device 70 can be used to assess coaptation height over a portion of the valve. Referring to FIG. 2C, the coaptation device shown in cross-section 70 is positioned between the anterior leaflet 12 and posterior leaflet 14 on a different portion of the mitral valve than is shown in FIG. 2B. It is important for the surgeon to know the coaptation height of a heart valve along the entire coaptation surface of the heart valve. Measurement of coaptation height over one portion of the valve may be adequate, but inadequate over another portion, and the latter may be the site of regurgitation of the valve. In the event that the coaptation measurement device 70 has a width less than the entire coaptation length of the valve, the coaptation device 70 can be moved to assess the valve in various locations to get an adequate or even complete picture of the coaptation height along the entire valve. For example, the coaptation measurement device 70 can have a maximum width of 18 mm to 23 mm in width to fit the mean diameter of the male aortic root. The coaptation measurement device 70 can be less than a typical valve width, for example less than 15 mm, less than 10 mm, or less than 5 mm, and be moved to assess the valve in various locations.

Figure 2D:
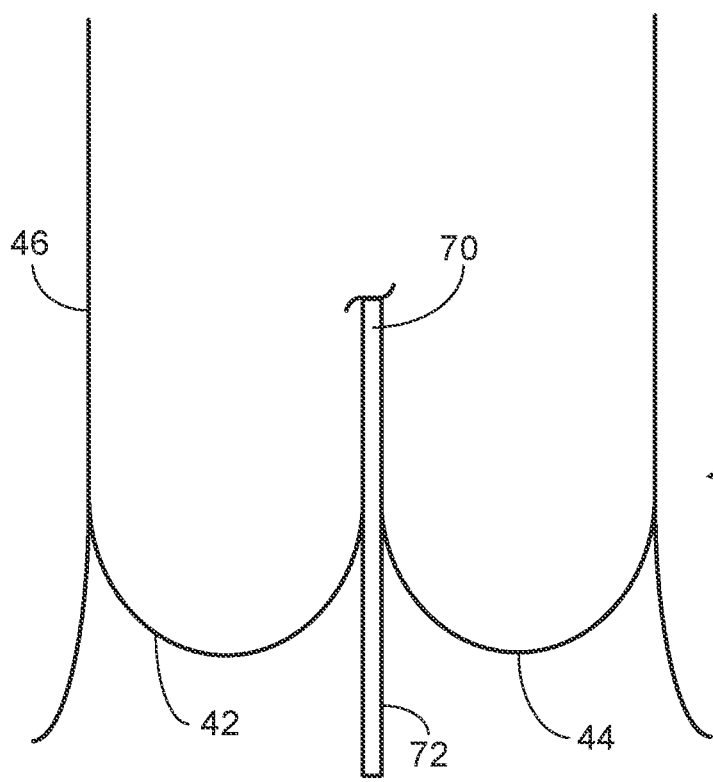
FIG. 2D is a cross-sectional view of an aortic valve and ascending aorta with the coaptation measurement device across the valve.

Referring to FIG. 2D, the root of the aorta is shown in cross-section with aortic valve leaflets 42 and 44 and aortic root wall 46. The coaptation measurement device 70 is positioned across the aortic valve with the distal end 72 residing within the left ventricle. The coaptation device may assess the coaptation height of the aortic valve leaflets in one or more portions of the valve. The coaptation device can be used to assess the valve during a catheterization procedure while the heart is beating during diastole when the heart is filling and the aortic valve is closed. The coaptation measurement device can also be used during an open procedure where a valve is assessed by filling the aortic root with fluid and inducing coaptation of the aortic valve leaflets in a pressurized or unpressurized fashion to assess the height of coaptation.

Figure 2E:
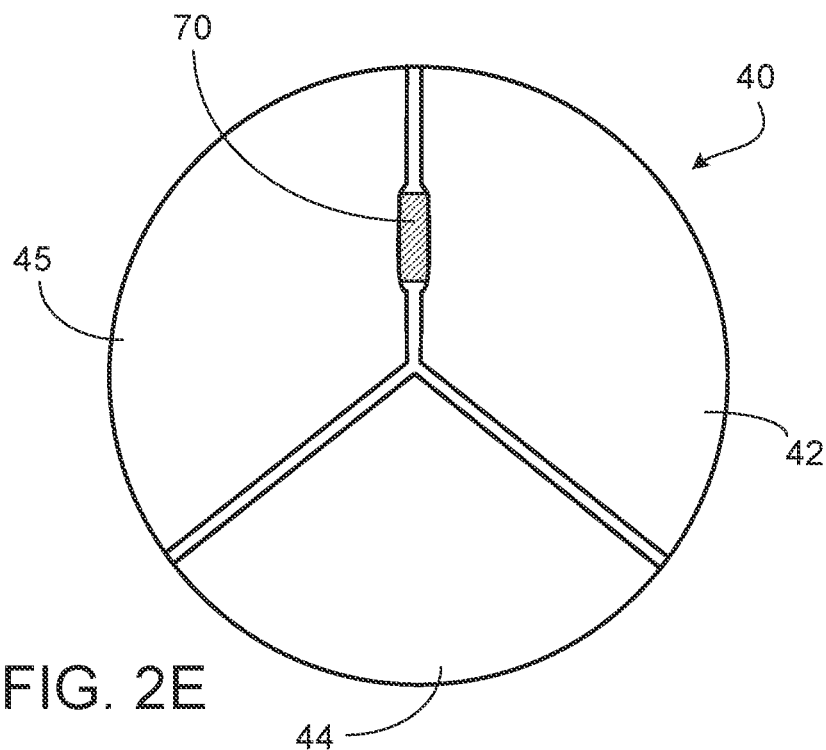
FIGS. 2E-2F are views of the aortic valve from the perspective of the aortic root with the coaptation measurement device across the valve.

Referring to FIG. 2E, the aortic valve 40 is shown with the leaflets 42, 44, and 45. The coaptation measurement device 70 is shown in cross-section positioned across the aortic valve between aortic valve leaflets 42 and 45, assessing a portion of the coaptation plane between the leaflets 42 and 45. The coaptation measurement device 70 may need to be moved to assess the coaptation height over several areas to assess the entire coaptation plane between two valve leaflets.

Figure 2F:
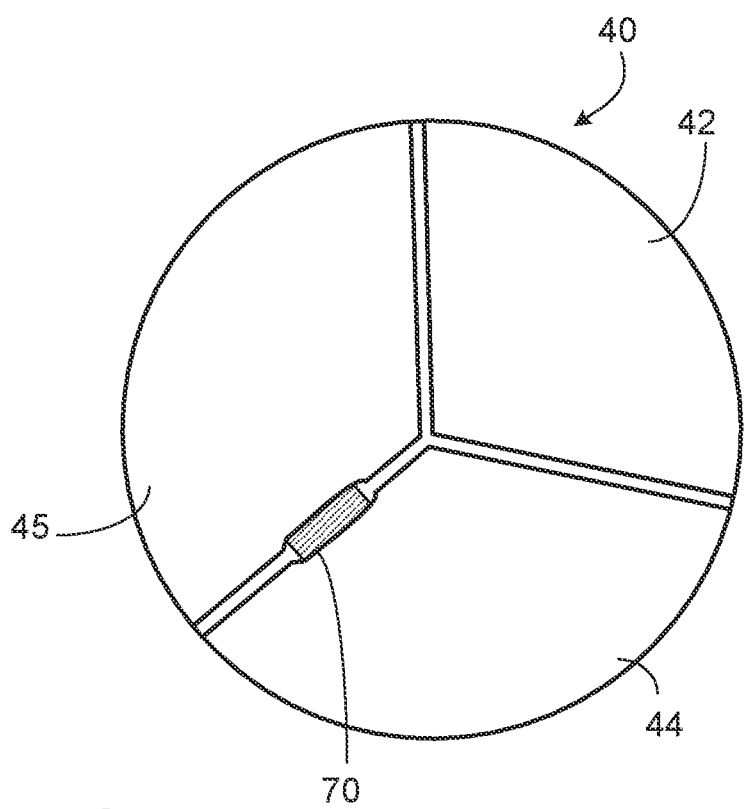

Referring to FIG. 2F, the aortic valve 40 is shown with the coaptation measurement 70 shown in cross-section position between two aortic valve leaflets 44 and 45. Certainly for tri-leaflet aortic valves and pulmonary valve or, less commonly for bi-leaflet or quadra-cusped aortic or pulmonary valves, assessment of multiple coaptation planes may be necessary to fully assess the coaptation height of the valve. The coaptation height of the valve will change with valve intervention. The device may be used multiple times throughout the interventional procedure or an open surgical procedure to reassess the coaptation height. The coaptation device 70 may be used to adjust the coaptation of the valve and calibrated to the desired amount by changing the anatomy. This could include a wide variety of interventions on any of the heart valves including changes to the valve subvalvar, valvar, annular, and even super annular aspects of the valve.

Figure 3A:
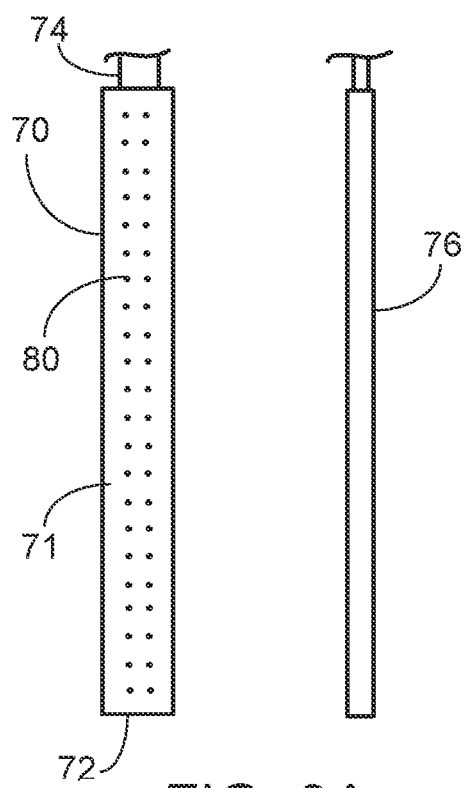
FIG. 3A-3C show the sensor portion of a coaptation measurement device.

Shown in FIG. 3A from the front and side is a coaptation measurement device 70 with a distal end 72 and a proximal connecting member 74. An important aspect of the coaptation measurement device 70 is the one or more sensors 80 positioned on the face 71 of the device along its length. The coaptation measurement device 70 may have an aspect ratio that is less than 1:1, giving a dimension of the thickness of the device 76 less than the width of the device. The smaller the thickness 76 of the device, the smaller is the distortion of the valve leaflets that will occur during assessment of coaptation height.

The one or more sensors 80 positioned along the face of the device 71 are used to assess the portion of the coaptation device that is adjacent to the space above the valve, the area of coaptation, and the space below the valve. For the different valves, the spaces above and below the valve represent different chambers of the heart or great vessels. In one embodiment of the invention, the sensor 80 consists of multiple resistor elements positioned across the device, creating an array of sensors. These resistor elements can be used with a computer interface to calculate the various resistances on the sensor and measure the coaptation height of an adjacent leaflet pressing against the sensor. The sensors 80 can also be a capacitor array forming a capacitive touch sensor capable of assessing the area of coaptation of the adjacent leaflet in the areas above and below the leaflet. These sensors can be temperature-sensing elements including thermistors to assess the temperature at the one or more spots along the length of the sensor. As the leaflets press against the sensor, a portion of the temperature sensor elements can be at a sufficiently different temperature than the other temperature elements to assess the coaptation area and height of adjacent valve leaflet. Typically, during open-heart surgery, the valve is assessed by injecting a fluid across the valve.

Monitoring the temperature changes as the valve leaflet coapt against the device can also be used to indicate the coaptation height. These sensors 80 can be optical elements that sense the presence of an adjacent structure with different optical density than blood or saline to assess the area of the sensor that is adjacent a portion of the heart valve leaflet for measurement of coaptation height. The sensor may be comprised of fiberoptic elements that may be coupled with a light source and camera or other sensor to receive and analyze the signals from the fiberoptic elements. The sensor may contain one or more than one different types of sensors described herein. For example, the sensor may measure force and have optical elements that sense optical changes. The force and optical data could be collaborated to provide data regarding the valve function. Alternatively, the sensor elements 80 can be ultrasound elements that send and receive ultrasound signals. The ultrasound signals delivered to the area adjacent a specific one of the sensors 80 can indicate an area of the sensor that is adjacent to a portion of a valve leaflet. The ultrasound elements can be in one of a variety of forms including but not limited to multiple individual crystals, arrays or sets of arrays of crystals or a piezoelectric film such as the film produced by Kureha (NY, NY).

The sensors 80 may contain a doping agent that transfers a substance to the valve leaflet where it contacts the sensor. The portion of the heart valve leaflet that touched the sensor then can be imaged to assess the coaptation height. An example would be a sensor 80 that has an ultraviolet substance attached, e.g., adhered, etched, or coated. After the coaptation device 70 is placed in proximity to the valve leaflets to be tested, the portions of the heart valve leaflet that touched sensors 80 would be imaged with a UV light and a camera capable of capturing UV spectrum light to detect the areas of the heart valve that touched the coaptation measurement device.

Figure 3B:
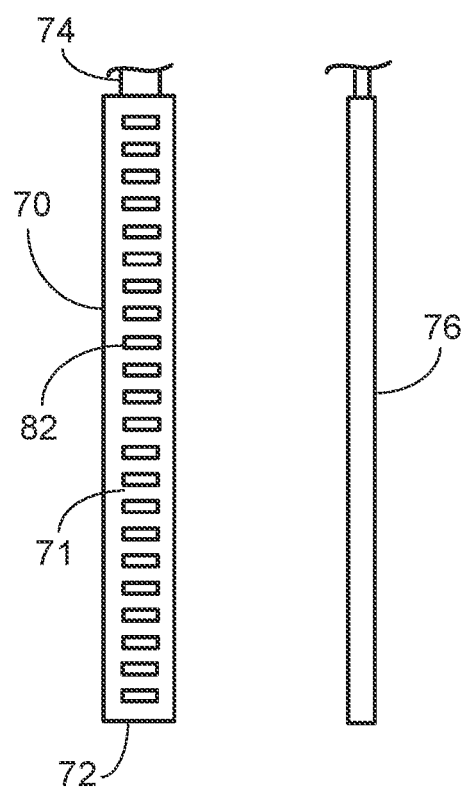

The sensor elements may be one or more rows of sensor elements (either along the length or along the width of the device) or an array of sensor elements across the face 71 of the device. There also may be sensor elements on the side of the device (e.g., along its width 76). In one embodiment, the sensor technology may be a matrix of a resistive touch sensor technology. Tekscan, Inc. (Boston, MA) has a representative resistive sensor technology suitable as a sensor for this device. This technology has a multiple array of resistive sensors that may be optimized to have distance between adjacent sensor points of less than a 2 mm or in another preferred embodiment less than 1 mm or in another preferred embodiment less than half a millimeter between one or more the sensors for points of measurement. Using this resistive array type sensor, the coaptation can be measured with adequate granularity to inform the surgeon of the adequacy of coaptation height or if additional adjustments need to be made. The resistive array sensor may be calibrated to measure the force of the leaflets on the sensor. The force measurements may be sensed many times per second creating a dynamic force map of the coaptation of the valve. The force measured across the sensor as the leaflets coapt can be translated into the coaptation height of the valve. The specifics of the leaflet forces across the coaptation height of the valve and how those forces develop dynamically during systole may be used to further characterize the function of the valve and understand current valve function and predict the valve function in the future. Analysis of the dynamic forces generated during coaptation may be displayed to the physician for additional decision making on the function of the valve in addition to the coaptation height. Referring to FIG. 3B, this coaptation measurement device 70 with distal portion 72 and proximal connecting member 74 may have one or more sensor elements 82 that extend across a portion of the face 71 of the sensor (e.g., extend across its width). The sensor elements may have a width of one-half or more of the width of the face 71 of the device.

Figure 3C:
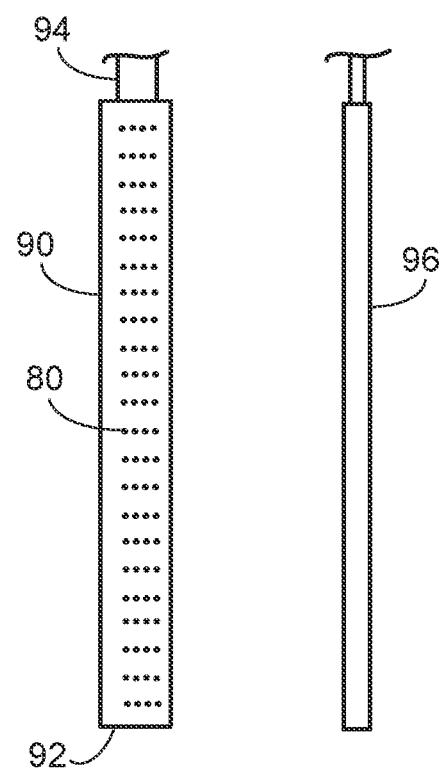

Referring to FIG. 3C, in one embodiment, device 90 has a distal portion 92 and proximal connecting member 94, one or sensor elements 80, and a cross-sectional thickness 96 minimal dimension. The material from which the sensors or the coaptation measurement device 90 is constructed maybe a thin, flexible material. The heart valve leaflet structures are thin and very flexible, especially heart valves in children and infants. A flexible coaptation measurement device 90 that can conform to the heart valve leaflets in the region of the coaptation to be assessed may facilitate accurate assessment of the coaptation height by eliminating or minimizing any distortion of the heart valve leaflets.

Figure 3D:
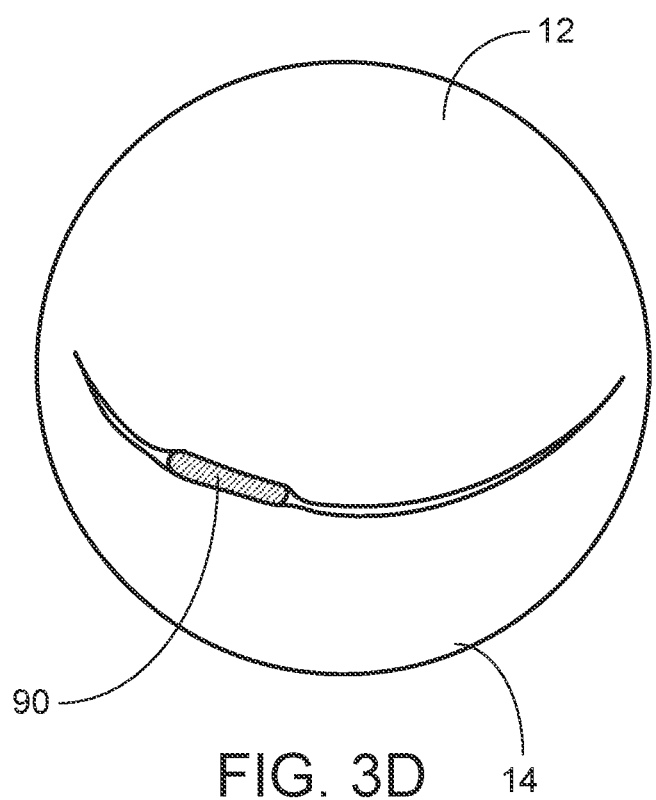
FIG. 3D is a view of the mitral valve from the perspective of the left atrium with a flexible coaptation measurement device across the valve.

Referring to FIG. 3D, a mitral valve is shown with leaflets 12 and 14, and a coaptation measurement device 90 shown in cross-section. The device 90 is flexible and is assessing the coaptation height between the anterior 12 and posterior 14 leaflets of the mitral valve around a portion of the valve, which is curved. The flexible coaptation measurement device 90 may allow a wider device to be used, which can assess the coaptation height over a wider coaptation surface of the valve.

Figure 4A:
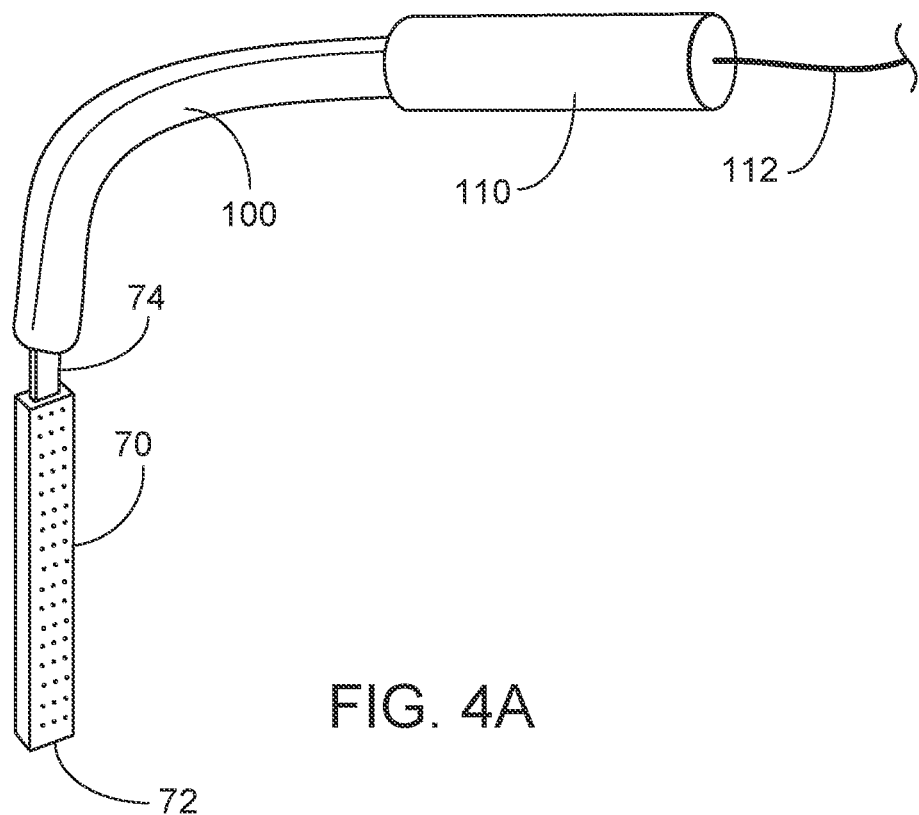
FIG. 4A is the distal portion of a coaptation measurement device with a proximal extension portion and a handle.

In FIG. 4A, the coaptation measurement device 70 has a distal end 72, and the proximal connecting member 74 is connected to an extension member 100, which connects to a handle 110. Flexible device 90 equivalently could be used. From handle 110, an electrical cord 112 extends to connect to a display and control element. The extension member 100 extends from the handle 110 and may be linear or nonlinear in shape. In one embodiment, the extension 100 maybe malleable or bendable so the surgeon could adjust the extension member 100 to position the sensor-containing portion of the coaptation measurement device 70 across the valve in a way so as to visualize but also comfortably hold so as to not distort the valve. The proximal connecting member 74 may be very short or could have some length (e.g., more than 1 cm, more than 2 cm, more than 5 cm) to maximize the ability for the surgeon to position the sensor portion across the valve in a way to visualize and not distort the valve.

Figure 4B:
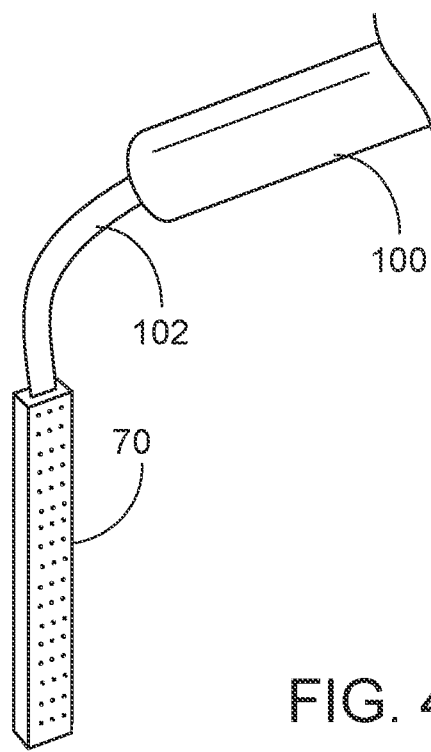
FIG. 4B is the distal portion of the coaptation measurement device with a proximal extension portion.

Referring to FIG. 4B, in another embodiment, the sensor-containing coaptation measurement device 70 has proximal connecting member 102 which is continuous with an extension member 100. This proximal connecting member 102 may be very flexible in nature. The goal is to minimize any impact of distortion of the valve on the assessment of the coaptation of the valve. In one embodiment, the proximal connecting member 102 may be a small cable carrying electrical signals from the sensor-containing portion of the device or it may be a thin ribbon-like structure that is flexible and confers very little force between extension 100 and distal coaptation measuring portion 70.

In another embodiment, the extension member 100 may be mounted to a chest retractor or other device such as a stand mounted to the operating room table. This arrangement would allow fixation of the device such that it could be set so the sensor-containing portion of the device 70 was across the valve without motion of distortion the valve during passive testing of the valve.

Figure 5:
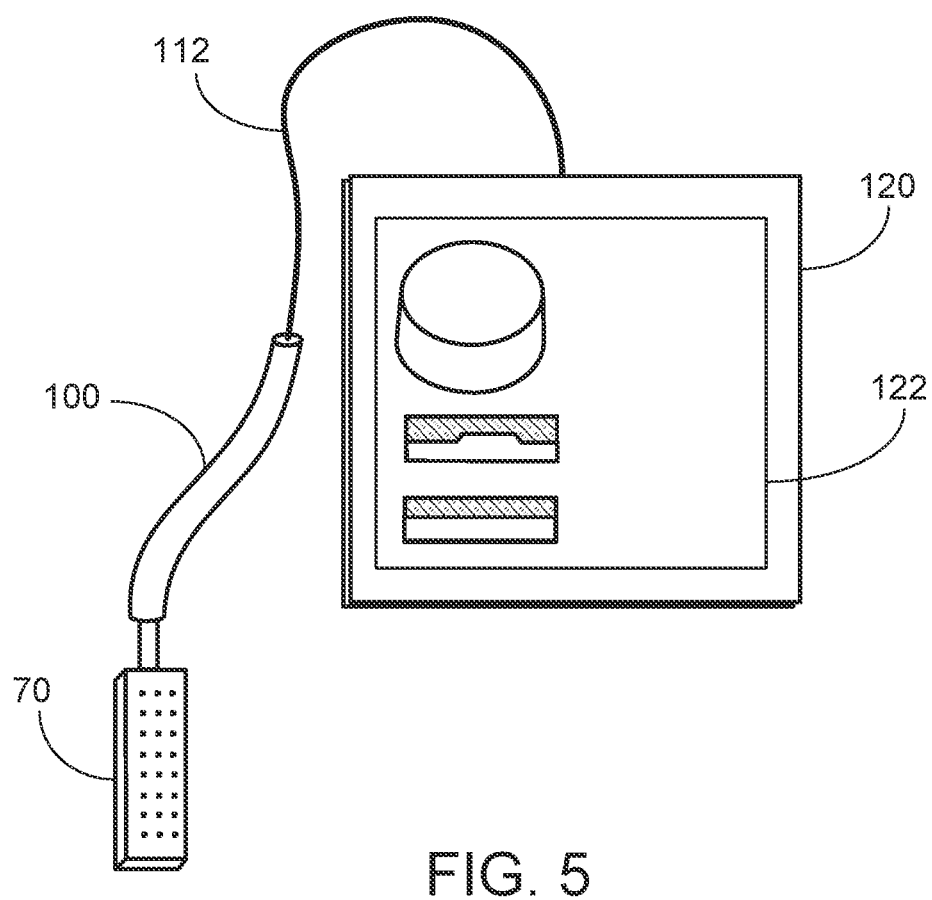
FIG. 5 is a coaptation measurement device with associated display screen.

Now referring to FIG. 5, the sensor-containing portion of the coaptation measurement device 70 is connected to the extension member 100. This extension member may have a separate handle portion at its proximal end. A cord or electrical wire-containing device 112 connects the device to computer interface 120 consisting of at least one screen 122. This interface 120 allows the surgeon or other operators to assess the coaptation height of any of the valves within the heart. The operator can select which valve is being assessed and mark the location of each assessment point on the valve. The operator can measure multiple coaptation heights for each valve. These multiple coaptation heights can then be graphically and numerically displayed on the screen 122. This display will give the surgeon or other operator a picture of coaptation heights across the entire coaptation length of the valve. Depending on the width of the sensor-containing portion of the coaptation measurement device, each coaptation measurement may be displayed either as a numerical height or as a range of heights in a graphical display of the coaptation length along the length of the sensor portion of the device.

The surgeon can utilize these data to make a decision to adjust the valve further with additional repair techniques to alter the coaptation height until the minimum goal coaptation is met. The coaptation height of one or more portions of the valve can be retested after additional valve repair maneuvers. The final testing of the valve coaptation can be completed prior to closing the heart. After the patient is weaned off cardiopulmonary bypass, the function of the valve can be assessed and compared to the measured coaptation height. It is expected that the coaptation heights obtained during intraoperative measurements will correspond to the valve function once the patient is off cardiopulmonary bypass and may be a predictor of the short and long-term valve function, with higher coaptation heights corresponding to better long-term valve function. For valve repair techniques that require fine adjustment including use of artificial cords, annuloplasty, and commissuroplasty maneuvers, the valve coaptation height measurement device may prove very useful for fine-tuning these various valve repair techniques for the best possible outcome.

Figure 6:
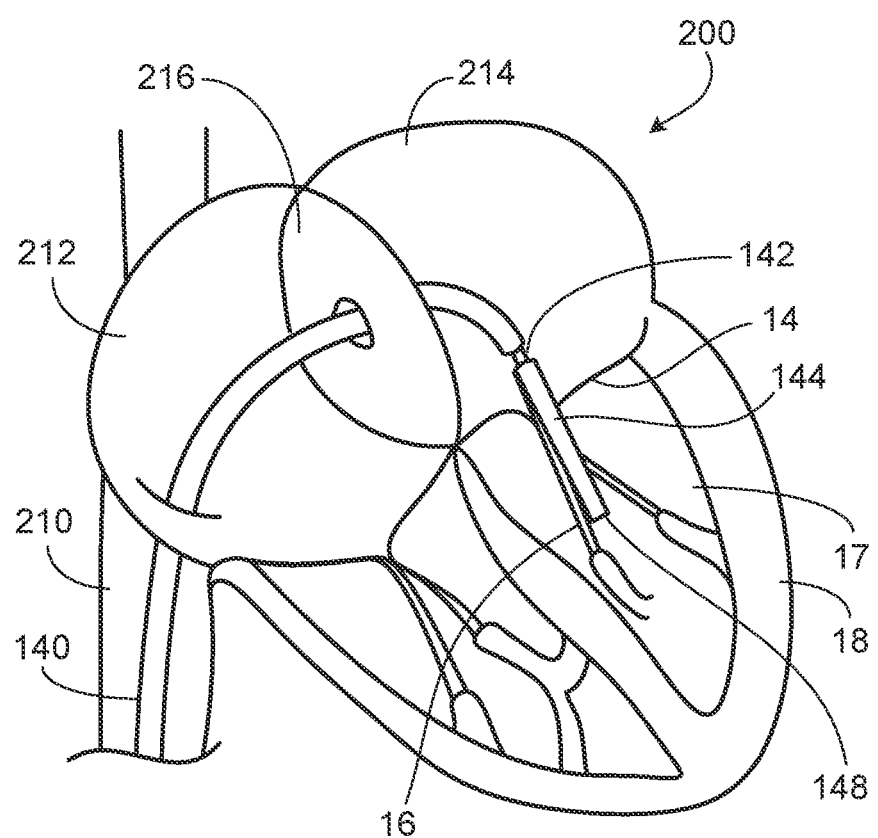
FIG. 6 is a cross-sectional image of a heart with a coaptation measurement catheter across the mitral valve.

Referring to FIG. 6, a cross-sectional image of the heart 200 is shown with inferior vena cava 210, right atrium 212, left atrium 214, and interatrial septum 216. The left ventricular wall 18 with left ventricle cavity 17 is shown with the mitral valve anterior leaflet 12 and posterior leaflet 14 with a coaptation measurement device 144 with a distal end 148 projecting through the mitral valve. A proximal connecting member 142 extends from the body of the catheter 140, which may enter the heart from the veins of the lower body. In one embodiment, the catheter may enter the femoral vein, pass through the inferior vena cava and right atrium, across the atrial septum through the left atrium and across the mitral valve. The catheter-based coaptation measurement devices allow for measurement of the mitral valve coaptation height while the patient's heart is beating during a catheterization procedure. There are multiple ways to access each of the heart valves during catheterization. This is one embodiment of a catheter path crossing the mitral valve. There may be other routes from the catheter to cross the mitral valve including via the superior vena cava. The tricuspid valve can also be assessed via the superior or inferior vena cava than across a tricuspid valve. The catheter can be extended through the right ventricle across the pulmonary valve to assess the coaptation height of the pulmonary valve. Additionally the catheter could be extended antegrade or retrograde across the aortic valve to assess the coaptation height of the aortic valve.

The use of the coaptation measurement device may be coupled with simultaneous transesophageal or transthoracic echocardiogram imaging to assess the exact location of the coaptation measurement device within the valve. With the combination of fluoroscopy as well as echocardiography, multiple coaptation heights for each valve could be assessed with known location of the coaptation device across the particular portion of the valve, thereby giving a picture of the coaptation heights across the coaptation surface for each valve of interest in a particular patient. Utilizing a catheter-based embodiment of the coaptation measurement device, the coaptation heights for a beating heart can be assessed. The physiologic conditions of the patient could also be altered to assess the valve under various conditions. This could include either giving volume to or diuresing a patient or adding or removing inotropic support as two examples of how the physiology of a patient can be changed to assess the function of the valve under different physiologic states during a catheterization procedure. The sensor portion of the coaptation measurement device 144 can be of sufficiently narrow width to fit through standard catheter sizes of 4, 6, 8, 10, 12, or 14 French. Alternatively, the sensor-containing portion of the catheter 144 can be in a rolled, folded, or otherwise reduced width state that can be expanded after it is advanced from within catheter 140 while the catheter is within the heart. The width of the sensor-containing portion of the catheter 144 may be wider than the width of the catheter 144 to allow measurement of coaptation height over a wider distance of a heart valve.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A coaptation measurement device comprising:
   an elongate sensor body at an end of a proximal connecting member; and
   a plurality of optical sensors in an array across a face of the sensor body,
   wherein each optical sensor of the plurality of optical sensors is configured to detect if a portion of a heart valve is in contact with the sensor, and
   wherein the plurality of optical sensors is configured to assess the valve coaptation height.

2. The coaptation measurement device of claim 1, wherein a plurality of optical sensors are arranged across a second face of the sensor body.

3. The coaptation measurement device of claim 1, wherein each optical sensor of the plurality of optical sensors has a width of a least a half of a width of the elongate sensor body.

4. The coaptation measurement device of claim 1, wherein the elongate sensor body is flexible.

5. The coaptation measurement device of claim 1, wherein the elongate sensor body is between several millimeters and several centimeters wide.

6. The coaptation measurement device of claim 1, wherein the plurality of optical sensors comprise optical elements that detect optical density of structures.

7. The coaptation measurement device of claim 1, wherein the plurality of optical sensors comprise fiberoptic elements.

8. The coaptation measurement device of claim 7, wherein the fiberoptic elements are coupled with a light source and camera or other sensor arranged to receive signals from the fiberoptic elements.

9. The coaptation measurement device of claim 1, further comprising one or more force sensors.

10. A method of measuring a coaptation height of a heart valve across a coaptation surface, the method comprising:
    placing a coaptation measurement device next to a coaptation surface, the coaptation device comprising:
    an elongate sensor body at an end of a proximal connecting member; and
    a plurality of optical sensors in an array across a face of the sensor body;
    wherein each optical sensor of the plurality of optical sensors is configured to detect if a portion of a heart valve is in contact with the sensor, and
    wherein the plurality of optical sensors is configured to assess the valve coaptation height;
    causing or allowing the valve to close;
    detecting by computer or a control element which optical sensors of the plurality of optical sensors detect that the respective sensor is in contact with the heart valve;
    determining, by the computer or the control element, a coaptation height from the sensors; and
    displaying the determined coaptation height.

11. The method of claim 10, further comprising repeating the placing, causing, detecting, and determining steps along one or more points on a coaptation surface.

12. The method of claim 10, further comprising displaying the determined coaptation height at each point on the coaptation surface as numerical values or as a graphical display.

13. The method of claim 10, wherein causing the valve to close comprises injecting fluid into a ventricle or aortic root.

14. The method of claim 10, wherein the plurality of optical sensors comprise optical elements that detect optical density of structures.

15. The method of claim 10, wherein the plurality of optical sensors comprise fiberoptic elements.

16. The method of claim 15, wherein the fiberoptic elements are coupled with a light source and camera or other sensor arranged to receive signals from the fiberoptic elements.

17. The method of claim 10, wherein the coaptation measurement device further comprises one or more force sensors.

18. The method of claim 17, wherein force data and optical data are used to determine valve function.

19. A coaptation measurement system, comprising:
    a coaptation measurement device, comprising:
    an elongate sensor body at an end of a proximal connecting member; and
    a plurality of optical sensors in an array across a face of the sensor body;
    wherein each optical sensor of the plurality of optical sensors is configured to detect if a portion of a heart valve is in contact with the optical sensor, and
    wherein the plurality of optical sensors is configured to assess the valve coaptation height;
    an extension member attachable to the proximal connecting member; and
    a handle connected to the extension member; and
    a display connected to the coaptation measurement device, wherein the display is configured to show information detected by the sensors of the coaptation measurement device.

20. The coaptation measurement system of claim 19, wherein the extension member is malleable or bendable.

21. The coaptation measurement system of claim 19, wherein a plurality of optical sensors are arranged across a second face of the sensor body.

22. The coaptation measurement system of claim 19, wherein each optical sensor of the plurality of optical sensors has a width of a least a half of the width of the elongate sensor body.

* * * * *